US00PP37257P2

(12) United States Plant Patent
Dirr et al.

(10) Patent No.: US PP37,257 P2
(45) Date of Patent: Feb. 10, 2026

(54) ***HYDRANGEA* PLANT NAMED 'SC-04-20'**

(50) Latin Name: *Hydrangea macrophylla*
Varietal Denomination: SC-04-20

(71) Applicant: Premier Introductions Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 19/186,008

(22) Filed: Apr. 22, 2025

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

(56) References Cited

PUBLICATIONS https://www.hortidaily.com/article/9644015/these-are-the-cultivate-24-exhibitors/ (Retrieved from the Internet on Jun. 18, 2025).*
https://www.gardencentermag.com/news/monrovia-new-cultivate-plants-2025/ (Retrieved from the Internet on Jun. 18, 2025).*
https://www.monrovia.com/seaside-serenade-pebble-beach-hydrangea.html?s (Retrieved from the Internet on Jun. 18, 2025).*

* cited by examiner

*Primary Examiner* — Susan Mccormick Ewoldt

(57) ABSTRACT

A new and distinct cultivar of *Hydrangea macrophylla* plant named 'SC-04-20', characterized by its glossy dark green foliage with red petioles, remontant (reblooming) trait, flowering on old wood and new growth of the season, rich deep rose mophead inflorescence in non-aluminum-based media and brilliant purplish-blue inflorescence in aluminum-based media, ruby red stems, foliar *Cercospora* resistance, and its compact, rounded habit with strong stems. The new cultivar is a *Hydrangea*, typically produced as an outdoor ornamental plant.

3 Drawing Sheets

Figure 1:
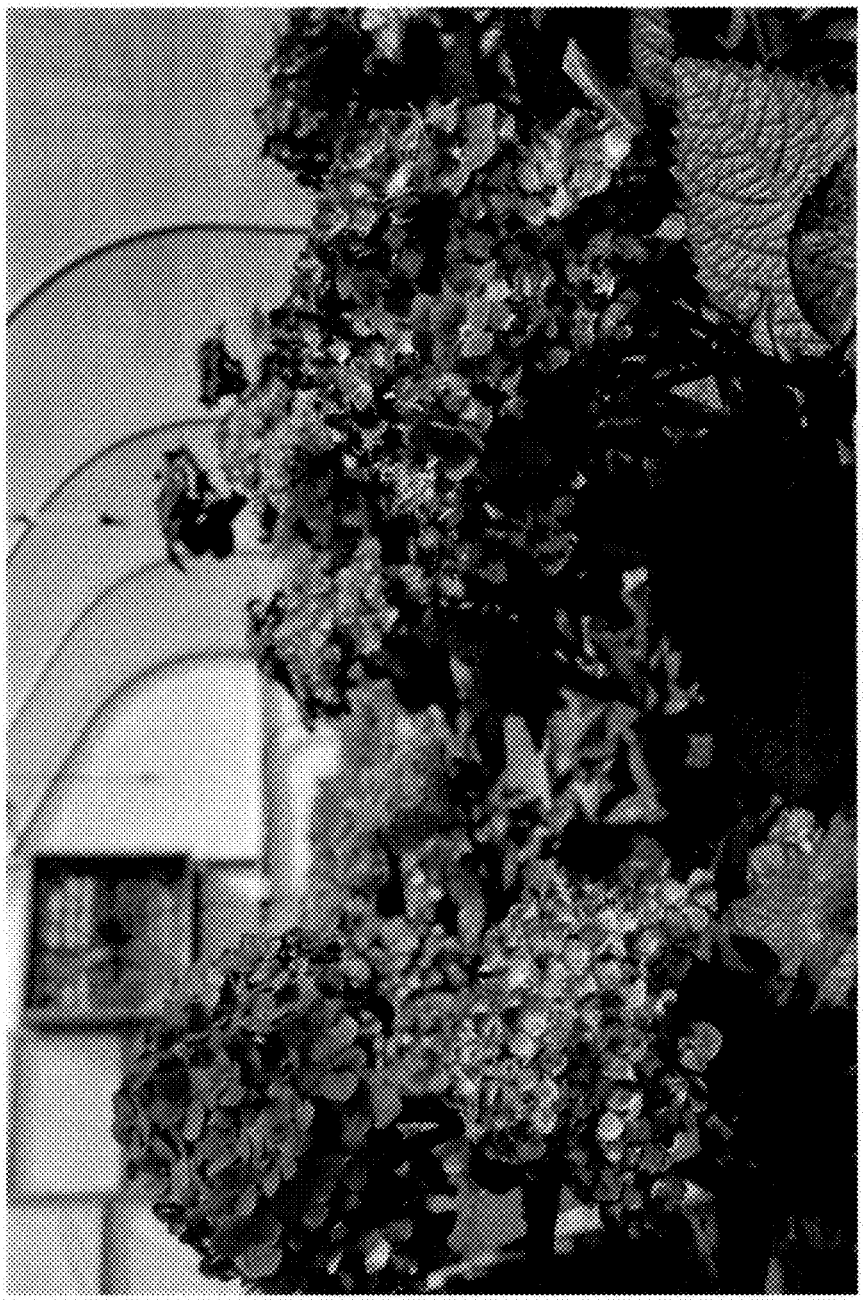

Latin name of the genus and species: *Hydrangea macrophylla.*

Variety denomination: 'SC-04-20'.

BACKGROUND OF THE INVENTION

The present invention relates to a new and distinct cultivar of *Hydrangea macrophylla*, a member of the Hydrangeaceae family, hereinafter referred to by its cultivar name 'SC-04-20'. This cultivar is grown primarily as an ornamental for landscape use and for use as a potted plant. The cultivar originated from an open pollination of *Hydrangea macrophylla* 'Bailmacfive', U.S. Plant Pat. No. 30,359, in Watkinsville, Georgia, in 2020, and was selected from the progeny by continued evaluation for growth habit, floral, and foliage characteristics.

'SC-04-20' has been asexually reproduced by softwood cuttings since 2020 in Watkinsville, Georgia. The characteristics of the cultivar have been stable and reproduced true to type in successive vegetative generations.

SUMMARY OF THE INVENTION

'SC-04-20' has not been observed under all possible environmental conditions. The phenotype may vary somewhat with changes in light, temperature, soil and rainfall without, however, any variance in genotype.

The following traits have been repeatedly observed and are determined to be the unique characteristics of 'SC-04-20.' These characteristics in combination distinguish 'SC-04-20' as a new and distinct *Hydrangea* cultivar:

1. Dark-green foliage with red (lower veins) and petioles.
2. Remontant (reblooming) trait, flowering on old wood and new growth of the season.
3. Rich deep rose mophead inflorescence in non-aluminum-based media and brilliant purplish-blue inflorescence in aluminum-based media.
4. Dark ruby red stems.
5. Compact, rounded growth habit with superior stem strength compared to other *Hydrangea.*

Parent Comparison

Plants of the new cultivar *Hydrangea* 'SC-04-20' can be compared to the seed parent variety in most horticultural characteristics, however, plants of 'SC-04-20' differ in the following:

1. 'SC-04-20' has rich deep rose flowers or brilliant purplish-blue flowers depending on the pH of the soil and available aluminum. 'Bailmacfive' has pink-red flowers or purple flowers depending on the pH of the soil and available aluminum.
2. 'SC-04-20' is more compact than 'Bailmacfive'.
3. The stems of 'SC-04-20' are stronger and rich ruby red compared to those of 'Bailmacfive'.

Commercial Comparison

Plants of the new cultivar *Hydrangea* 'SC-04-20' can be compared to the commercial variety *Hydrangea* 'PIIHM-ll', U.S. Plant Pat. No. 25,566. Plants of 'SC-04-20' are similar to plants of 'PIIHM-ll' in most horticultural characteristics, however, plants of 'SC-04-20' differ in the following:

1. Internodes of 'SC-04-20' are approximately 50% shorter than internodes of this comparator.
2. Plants of 'SC-04-20' are more compact than plants of this comparator.
3. Inflorescences of 'SC-04-20' are on average 1 to 1.5 larger in diameter than inflorescences of this comparator.
4. Stems of 'SC-04-20' are stronger than stems of this comparator.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea*.

FIG. 1: Shows 'SC-04-20', a two-year-old plant, with aluminum, showing the flower color.

Figure 2:
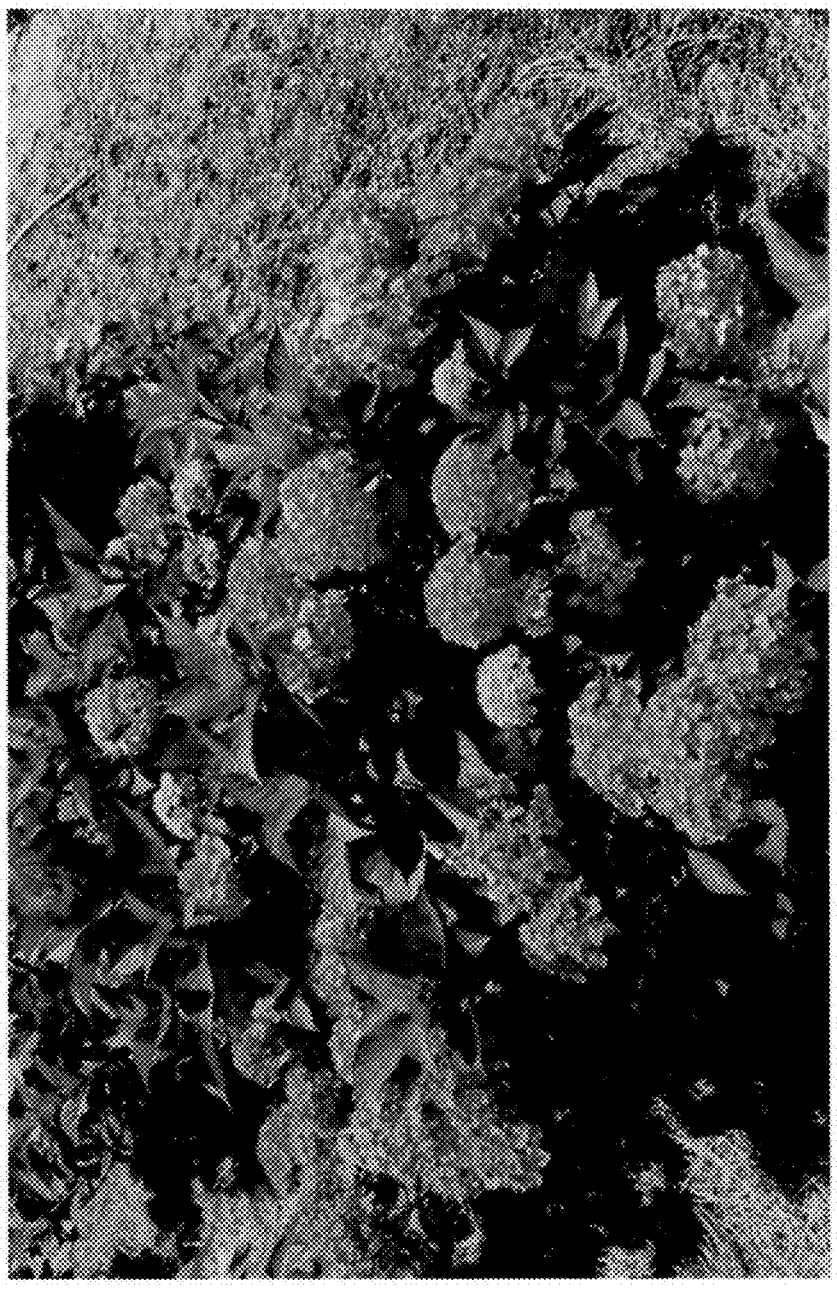

FIG. 2: Shows 'SC-04-20', the original plant, in the ground, 4-years-old, showing habit (compactness) and flower color in non-aluminum soil.

Figure 3:
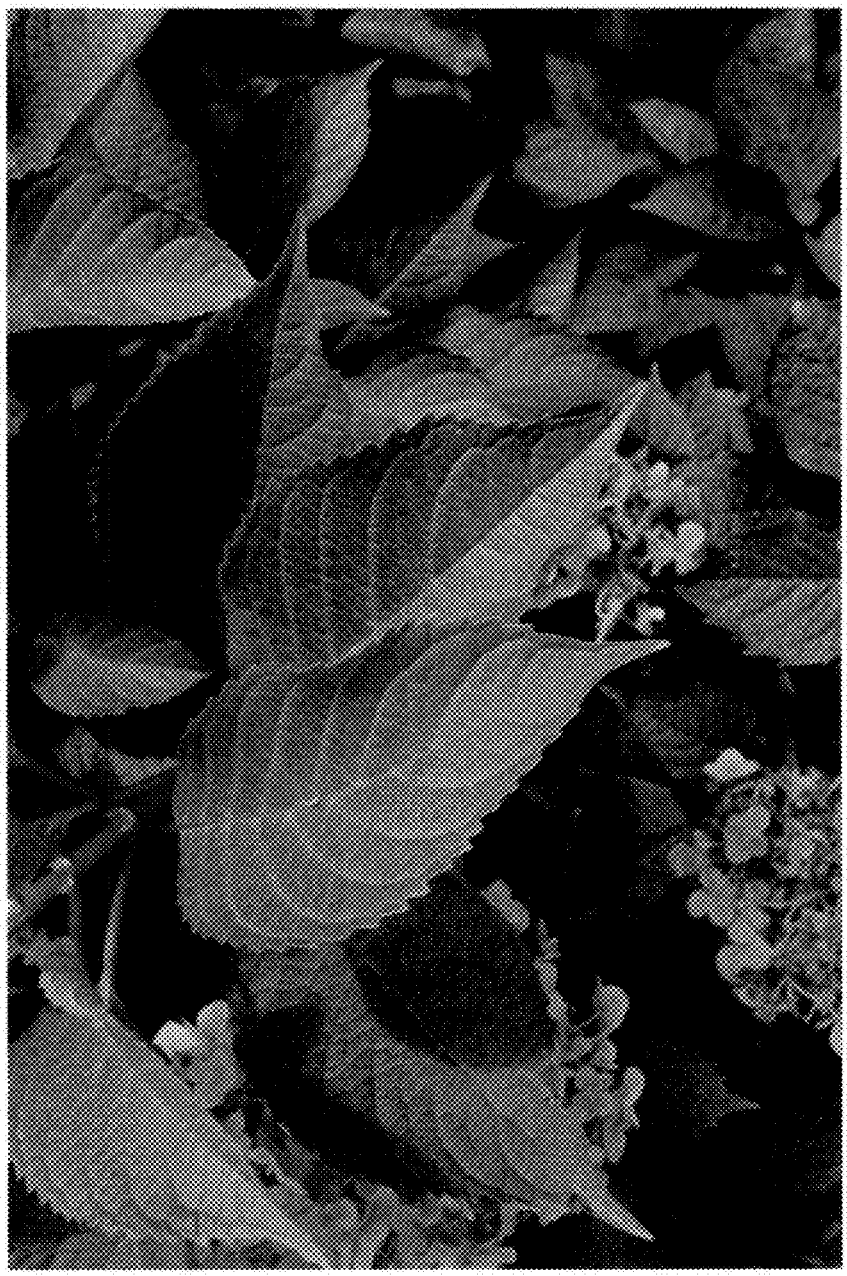

FIG. 3: Shows the original plant, 4-years-old, 'SC-04-20', stem and petiole color.

DETAILED BOTANICAL DESCRIPTION

In the following description, color references are made to The Royal Horticultural Society Colour Chart, 2015 Edition, except where general terms of ordinary dictionary significance are used. Plants used for the description were grown in ground under 50% shade under outdoor conditions in a nursery in Watkinsville, GA. Plants were about four years old when the description was recorded. Two groups of plants were used for the description to describe the flower colors with and without aluminum. The first group was grown in a medium consisting of composted pine bark, with no aluminum present and a pH of 5.4. The second group was grown in a medium consisting of composted pine bark that was amended with 60 grams of aluminum sulphate and a pH of 5.3. Aluminum only affects flower (sepal) color. Therefore, colors with and without aluminum are only specified for floral parts.

Botanical classification: *Hydrangea macrophylla* 'SC-04-20'.

Propagation:

*Typical Method*—Vegetatively by stem cuttings.

*Root Initiation*—Approximately 14 days at 32° C.

*Time to Produce Rooted Cutting*—About 3 months at 32° C. during summer.

*Time to Produce a Finished Crop*—In a 11.4 L container potted with a 0.041 L liner pot, about 9 months.

*Roots*—Root description: numerous, fine, fibrous and well-branched. Color: RHS White NN155A.

Plant:

*Plant Type*—Rounded and spreading deciduous shrub.

*Height*—86 cm.

*Plant Spread*—127 cm.

*Age of Plant Described*—Approximately 5 years.

*Branching Characteristics*—Freely-branching. Pinching enhances branching. Number of Lateral Branches: About 8 per plant.

*First Year Stems*—Length: 30 cm. Width: 3 mm. Color: RHS Red-Orange 175B. Shape: Round. Strength: Flexible. Texture: Smooth.

*Second Year Stems*—Length: 40 cm. Width: 6 mm. Color: RHS Brown 199C. Shape: Round. Strength: Easily broken. Texture: Woody.

*Lenticels*—Quantity: 20 to 30 per internode; 4 internodes per stem. Color: RHS Brown 165A on one-year-old stem.

*Vegetative Buds*—Arrangement: Opposite. Shape: Ovoid. Length: 2 mm. Width: 1 mm. Color: RHS Red-Orange 175B.

Foliage:

*Leaf*—Arrangement: Opposite, simple. Shape: Ovate. Length: 9 cm. Width: 8 cm. Apex: Acuminate. Base: Cuneate. Margin: Serrate. Texture of top surface: Glabrous. Texture of bottom surface: Glaucescent. Color: Young foliage upper side: RHS Yellow-Green 147A. Young foliage under side: RHS Yellow-Green 146B. Mature foliage upper side: RHS Green 137A and NN137A. Mature foliage, under side: RHS Green 138B.

Venation: Type: Pinnate. Color: Young, upper side: Midrib RHS Red 183A; lateral rib Green NN137A. Young, under side: Midrib and lateral rib RHS Green 138A. Mature, upper side: Midrib RHS Red 183A; lateral rib Green NN137A. Mature, under side: Midrib and lateral rib RHS Green 138A.

*Petiole*—Length: 3 cm. Width: 3 mm. Color: Upper side: RHS Red 185A. Under side: RHS Red 185A. Texture: Smooth, glabrous. Petiole is grooved on upper side, and crescent-shaped in cross section.

Inflorescence:

*Natural flowering season*—Early summer to mid-frost in fall. The inflorescence is effective for about 8 weeks.

*Inflorescence Type*—Mophead. Height: 8 cm. Diameter: 14 cm.

*Fragrance*—None.

*Bud*—Bud Length: 6 mm. Bud Diameter: 4 mm. Bud Shape: Ovoid. Bud Color: Prior to opening: RHS Yellow-Green 145B. When opening, with aluminum: RHS Purplish-Blue 100C. When opening, without aluminum: RHS Purple 73D.

*Sterile Florets*—Flowers Per Inflorescence: About 160. Shape: Ovoid. Tip: Obtuse. Base: Acute. Margin: Entire. Diameter: 1.5 to 2 cm.

*Sepals*—Number per Flower: 4. Length: 1 cm. Width: 1 cm. Texture: Upper side: Smooth. Under side: Smooth. Color: At maturity, with aluminum: Upper side: RHS Blue 98B. Under side: RHS Purplish-Blue 97C. At maturity, without aluminum: Upper side: RHS Purplish-Pink N66A. Under side: RHS Purplish-Pink N66C. Aged sepals, with aluminum: Upper side: RHS Purplish-Blue 96D. Under side: RHS Purplish-Blue 97C. Aged sepals, without aluminum: Upper side: RHS Red-Purple 70B. Under side: RHS Purplish-Pink 68C.

*Fertile Flowers*—Flowers Per Inflorescence: About 40.

*Petals*—Number per Flower: 5. Shape: Ovate. Tip: Acuminate. Base: Truncate. Margin: Entire. Length: 4 mm. Width: 2 mm. Texture: Smooth, no pubescence. Color: With aluminum, upper side: RHS Purplish-Blue 96D. With aluminum, under side: RHS Purplish-Blue 94C. Without aluminum, upper side: RHS Red-Purple N74D. Without aluminum, under side: RHS Purple 75D.

*Peduncle*—Length: 4.5 cm. Diameter: 4 mm. Angle: Upright. Strength: Moderately strong and flexible. Color: RHS Red-Orange 175B.

*Pedicel*—Length: 1.5 cm. Diameter: 1 mm. Angle: 45° from vertical. Strength: Moderately strong and flexible. Texture: Smooth. Color: With aluminum: RHS Purplish-Blue 96A. Without aluminum: RHS Red 185A.

Reproductive Organs:

*Stamens*—Number: 4 to 5 per flower. Filament Length: 3 mm. Filament Color: With aluminum: RHS Purplish-Blue 94B. Without aluminum: RHS Red-Purple N74A.

*Anthers*—Length: About 1 mm. Width: 0.5 mm. Color: With aluminum: RHS Purplish-Blue 94B. Without aluminum: RHS Red-Purple N74B. Pollen Amount: Moderate. Pollen Color: RHS Yellow-White 155A.

*Pistil*—Number: 1. Length: 3 mm. Width: 1.5 mm. Color: With aluminum: RHS Red-Purple N74B. Without aluminum: RHS Purple-Red 63B.

*Stigma*—Number: 2 or 3. Shape: Round. Color: With aluminum: RHS Purplish-Blue 94A. Without aluminum: RHS Red-Purple N74B. Style Length: 2 mm. Style Shape: Tubular. Style Color: With aluminum: RHS Purplish-Blue 94A. Without aluminum: RHS Red-Purple N74A.

Other Characteristics:

*Fruit*—Number: Varies widely. Shape: Ovoid. Length: 3 mm. Width: 2 mm. Color: During ripening: Near RHS Purplish-Pink 54B. At maturity: Near RHS Brown 200C.

*Seeds*—Number: About 25 seeds per capsule. Shape: Round. Length: 0.5 mm. Width: 0.5 mm. Color: Near RHS Brown 199B.

*Disease Resistance*—High Cercospora resistance compared to 'Bailmacfive'. Susceptibility or resistance to diseases beyond that typically found in other *Hydrangea macrophylla* plants has not been observed.

*Drought Tolerance and Cold Tolerance*—USDA Hardiness Zone Map (2012): Zones 7-9.

What is claimed is:

1. A new and distinct cultivar of Hydrangea plant named 'SC-04-20' as herein illustrated and described.

* * * * *